United States Patent
Kimura et al.

(10) Patent No.: US 10,254,352 B2
(45) Date of Patent: Apr. 9, 2019

(54) CONDUCTIVITY DISTRIBUTION DERIVATION METHOD AND CONDUCTIVITY DISTRIBUTION DERIVATION DEVICE

(71) Applicants: National University Corporation Kobe University, Hyogo (JP); Integral Geometry Science Inc., Hyogo (JP)

(72) Inventors: Kenjiro Kimura, Hyogo (JP); Noriaki Kimura, Hyogo (JP)

(73) Assignees: NATIONAL UNIVERSITY CORPORATION KOBE UNIVERSITY, Hyogo (JP); INTEGRAL GEOMETRY SCIENCE INC., Hyogo (JP)

( * ) Notice: Subject to any disclaimer, the term of this patent is extended or adjusted under 35 U.S.C. 154(b) by 100 days.

(21) Appl. No.: 15/124,874
(22) PCT Filed: Mar. 11, 2015
(86) PCT No.: PCT/JP2015/001344
§ 371 (c)(1),
(2) Date: Sep. 9, 2016
(87) PCT Pub. No.: WO2015/136931
PCT Pub. Date: Sep. 17, 2015

(65) Prior Publication Data
US 2017/0016963 A1  Jan. 19, 2017

(30) Foreign Application Priority Data
Mar. 12, 2014  (JP) .................. 2014-049513

(51) Int. Cl.
G01R 31/36 (2006.01)
G01N 27/72 (2006.01)

(52) U.S. Cl.
CPC ......... *G01R 31/3662* (2013.01); *G01N 27/72* (2013.01); *G01R 31/3651* (2013.01)

(58) Field of Classification Search
CPC . G01R 31/3662; G01R 31/3651; G01N 27/72
(Continued)

(56) References Cited

U.S. PATENT DOCUMENTS 7,250,757 B1 *  7/2007  Tiernan ............. G01N 27/9046
                                                                    324/228
7,759,931 B2     7/2010  Tsukada et al.
(Continued)

FOREIGN PATENT DOCUMENTS

JP  2003-222664  8/2003
JP  2009-74953   4/2009
(Continued)

OTHER PUBLICATIONS

G. Moritz, Eddy currents in accelerator magnets, 2011, GSI, Darmstadt, Germany, pp. 1-38.*
(Continued)

*Primary Examiner* — Eman A Alkafawi
(74) *Attorney, Agent, or Firm* — Wenderoth, Lind & Ponack, L.L.P.

(57) ABSTRACT

A conductivity distribution derivation method for deriving a conductivity distribution within a battery having an electrode plate that is flat includes: obtaining magnetic field information indicating a magnetic field; and deriving, based on a plurality of relational expressions which (i) an x component of a magnetic field vector in an x direction parallel to the electrode plate, (ii) a y component of the magnetic field vector in a y direction parallel to the electrode plate and perpendicular to the x direction, (iii) the conductivity distribution on a two-dimensional plane parallel to the electrode plate, and (iv) an electric potential distribution on a two-dimensional plane parallel to the electrode plate satisfy, the conductivity distribution that satisfies the plurality of relational expressions with respect to the magnetic field information.

6 Claims, 6 Drawing Sheets

(58) Field of Classification Search
USPC .......................................................... 702/63
See application file for complete search history.

(56) References Cited

U.S. PATENT DOCUMENTS

| | | | |
|---|---|---|---|
| 8,536,862 B2 | 9/2013 | Kimura et al. | |
| 2005/0012496 A1* | 1/2005 | Taniguchi | G01R 15/181 |
| | | | 324/117 R |
| 2005/0104585 A1* | 5/2005 | Bilik | G01N 27/9033 |
| | | | 324/240 |
| 2008/0211492 A1 | 9/2008 | Tsukada et al. | |
| 2010/0219819 A1 | 9/2010 | Kimura et al. | |
| 2012/0148880 A1 | 6/2012 | Schaefer et al. | |
| 2014/0081584 A1 | 3/2014 | Kimura | |

FOREIGN PATENT DOCUMENTS

| | | |
|---|---|---|
| JP | 2009-229337 | 10/2009 |
| JP | 2012-524385 | 10/2012 |
| WO | 2006/109382 | 10/2006 |
| WO | 2008/123432 | 10/2008 |
| WO | 2010/121787 | 10/2010 |
| WO | 2012/153496 | 11/2012 |

OTHER PUBLICATIONS

International Search Report dated Jun. 2, 2015 in corresponding International Application No. PCT/JP2015/001344.

Yuki Mima et al., "Development of Tunneling Magnetoresistance Microscope With Electromagnetic Field Reconstruction and Its Application to Visualizing Electric Current Inside Battery", Dai 54 Kai Denchi Toronkai Koen Yoshishu, 2013. 10. 6, p. 423—with full English translation.

Kenjiro Kimura et al., "Developments of Electromagnetic Field Reconstruction Method and Scanning Tunneling Magnetoresistance Microscope", Electronic Packaging Technology, Jan. 20, 2012, vol. 28, No. 2, p. 16-20—with full English translation.

Chikayoshi Sumi et al., "Determination of the spatial distribution of a physical parameter from the distribution of another physical variable—a differential inverse problem", J. Appl. Phys., Jul. 1996, vol. 80, No. 1, p. 1-7.

Bradley J. Roth et al., "Using a magnetometer to image a two-dimensional current distribution", Journal of Applied Physics, Jan. 1989, vol. 65, No. 1, p. 361-372.

* cited by examiner

CONDUCTIVITY DISTRIBUTION DERIVATION METHOD AND CONDUCTIVITY DISTRIBUTION DERIVATION DEVICE

TECHNICAL FIELD

The present invention relates to a conductivity distribution derivation method and a conductivity distribution derivation device for deriving a conductivity distribution within a battery.

BACKGROUND ART

In recent years, dendrites that grow in a lithium battery have been considered problematic because they may cause a short circuit within the battery, explosion of the battery, or the like. Therefore, effective inspection methods for preventing such a short circuit or the like have been researched and developed. In this regard, Patent Literature (PTL) 1 discloses a method for examining the condition of a battery by using high-brightness X-ray, visible light, or ultrasound waves.

CITATION LIST

Patent Literature

[PTL 1] Japanese Unexamined Patent Application Publication (Translation of PCT Application) No. 2012-524385

SUMMARY OF INVENTION

Technical Problem

However, visible light and microwaves (magnetic resonance imaging: MRI) are less likely to pass through a metal collector of a battery. Therefore, examining the condition of the inside of a battery with visible light or microwaves is difficult.

The condition of the inside of a battery can be examined with high-brightness X-ray, and it is possible to use high-brightness X-ray to, for example, inspect for foreign materials in a battery, but inspecting for an electrical failure within a battery with high-brightness X-ray is difficult. Therefore, inspecting for a short circuit or the like within a battery with any of high-brightness X-ray, visible light, and microwaves is difficult.

In light of the foregoing, an object of the present invention is to provide a conductivity distribution derivation method and a conductivity distribution derivation device by which a conductivity distribution that is effective in inspecting for a short circuit or the like within a battery can be appropriately derived.

Solution to Problem

For example, a conductivity distribution derivation method according to an aspect of the present invention is a conductivity distribution derivation method for deriving a conductivity distribution within a battery having an electrode plate that is flat, and includes: obtaining magnetic field information indicating a magnetic field; and deriving, based on a plurality of relational expressions which (i) an x component of a magnetic field vector in an x direction parallel to the electrode plate, (ii) a y component of the magnetic field vector in a y direction parallel to the electrode plate and perpendicular to the x direction, (iii) the conductivity distribution on a two-dimensional plane parallel to the electrode plate, and (iv) an electric potential distribution on a two-dimensional plane parallel to the electrode plate satisfy, the conductivity distribution that satisfies the plurality of relational expressions with respect to the magnetic field information.

With this, a conductivity distribution can be appropriately derived based on the relationship between the magnetic field, the conductivity distribution, and the like. Therefore, it is possible to appropriately inspect for an electrical failure such as a short circuit or the like within a battery.

For example, the plurality of relational expressions may include: (i) a first relational expression representing a relationship between the x component of the magnetic field vector, the conductivity distribution, and the electric potential distribution; (ii) a second relational expression representing a relationship between the y component of the magnetic field vector, the conductivity distribution, and the electric potential distribution; and (iii) a third relational expression representing a relationship between the conductivity distribution and the electric potential distribution, and in the deriving, the conductivity distribution may be derived based on the first relational expression, the second relational expression, and the third relational expression.

With this, a conductivity distribution can be appropriately derived based on three relational expressions that are based on the relationship between the magnetic field, the conductivity distribution, and the like.

For example, in the deriving, the conductivity distribution that is represented using σ may be derived based on the first relational expression that is represented by [Math. 2], the second relational expression that is represented by [Math. 3], and the third relational expression that is represented by [Math. 4], $$\varphi \quad \text{[Math. 1]}$$

$$\Delta H_x = h_T^{-1} h \partial_y \{\sigma(x,y)\varphi(x,y)\}\delta(z-z_0) - \sigma_0 h\{\partial_y \varphi(x,y)\}\delta'(z-z_0) \quad \text{[Math. 2]}$$

$$\Delta H_y = -h_T^{-1} h \partial_x \{\sigma(x,y)\varphi(x,y)\}\delta(z-z_0) - \sigma_0 h\{\partial_x \varphi(x,y)\}\delta'(z-z_0) \quad \text{[Math. 3]}$$

$$\partial_x^2 \varphi + \partial_y^2 \varphi = (\sigma_0 h h_T)^{-1}\sigma(x,y)\varphi(x,y) \quad \text{[Math. 4]}$$

where x denotes a coordinate in the x direction, y denotes a coordinate in the y direction, z denotes a coordinate in a z direction perpendicular to the x direction and the y direction, $z_0$ denotes a coordinate of the electrode plate in the z direction, $H_x$ denotes the x component of the magnetic field vector, $H_y$ denotes the y component of the magnetic field vector, h denotes a thickness of the electrode plate in the z direction, $h_T$ denotes a distance between one pair of electrode plates including the electrode plate, $\sigma_0$ denotes conductivity of the electrode plate, σ denotes the conductivity distribution, [Math. 1] denotes the electric potential distribution, δ denotes a delta function, δ' denotes a differential of the delta function, $\partial_x$ denotes a partial differential with respect to x, and $\partial_y$ denotes a partial differential with respect to y.

With this, a conductivity distribution can be appropriately derived based on three relational expressions that have been specifically determined as mathematical expressions.

For example, in the deriving, the conductivity distribution may be derived based on a fourth relational expression represented by [Math. 7] and a fifth relational expression represented by [Math. 8], the fourth relational expression being based on the first relational expression, the second relational expression, and the third relational expression, the fifth relational expression being based on the third relational expression,

[Math. 5]

$$\varphi$$

[Math. 6]

$$\tilde{\varphi}$$

[Math. 7]

$$\tilde{\varphi}(k_x, k_y) = \frac{2\{ik_y Q_x(k_x, k_y, z_0) - ik_x Q_y(k_x, k_y, z_0)\}}{hk^2 \sigma_0 (hk - 1)}$$

[Math. 8]

$$\sigma(x, y) = hh_T \sigma_0 \frac{(\partial_x^2 + \partial_y^2)\varphi}{\varphi}$$

where $k_x$ denotes a wave number in the x direction, $k_y$ denotes a wave number in the y direction, $Q_x$ denotes a function of $H_x$ obtained through a Fourier transform with respect to the x direction and the y direction, $Q_y$ denotes a function of $H_y$ obtained through a Fourier transform with respect to the x direction and the y direction, and [Math. 6] denotes a function of [Math. 5] obtained through a Fourier transform with respect to the x direction and the y direction.

With this, a conductivity distribution can be appropriately derived from the magnetic field according to a predetermined mathematical expression.

For example, in the deriving, the conductivity distribution may be derived based on the fourth relational expression, the fifth relational expression, a sixth relational expression represented by [Math. 9], and a seventh relational expression represented by [Math. 10],

[Math. 9]

$$Q_x(k_x, k_y, z_0) = \frac{1}{2}\left\{Q_x(k_x, k_y, z_1) - \frac{1}{\sqrt{k_x^2 + k_y^2}}\partial_z Q_x(k_x, k_y, z_1)\right\}e^{(z_1 - z_0)\sqrt{k_x^2 + k_y^2}}$$

[Math. 10]

$$Q_y(k_x, k_y, z_0) = \frac{1}{2}\left\{Q_y(k_x, k_y, z_1) - \frac{1}{\sqrt{k_x^2 + k_y^2}}\partial_z Q_y(k_x, k_y, z_1)\right\}e^{(z_1 - z_0)\sqrt{k_x^2 + k_y^2}}$$

where $z_1$ denotes a coordinate in the z direction outside the battery, and $\partial_z$ denotes a partial differential with respect to z.

With this, a conductivity distribution within a battery can be appropriately derived from the magnetic field outside the battery according to a predetermined mathematical expression.

For example, in the deriving, the x component of the magnetic field vector and the y component of the magnetic field vector may be derived based on a candidate for the conductivity distribution, a candidate for the electric potential distribution, and the plurality of relational expressions, and when the x component derived and the y component derived fit the magnetic field indicated by the magnetic field information, the conductivity distribution may be derived by determining the candidate for the conductivity distribution as the conductivity distribution.

With this, a conductivity distribution that fits a plurality of relational expressions can be derived through the repetition of the same or similar computation.

For example, in the deriving, the conductivity distribution may be derived using a general purpose graphics processing unit (GPGPU) for using an image processing device in an application different from image processing.

With this, a conductivity distribution can be derived at high speed on the basis of GPGPU which is capable of performing the same or similar computation at high speed.

For example, a conductivity distribution derivation device according to an aspect of the present invention is a conductivity distribution derivation device for deriving a conductivity distribution within a battery having an electrode plate that is flat, and includes: an obtainment unit configured to obtain magnetic field information indicating a magnetic field; and a derivation unit configured to derive, based on a plurality of relational expressions which (i) an x component of a magnetic field vector in an x direction parallel to the electrode plate, (ii) a y component of the magnetic field vector in a y direction parallel to the electrode plate and perpendicular to the x direction, (iii) the conductivity distribution on a two-dimensional plane parallel to the electrode plate, and (iv) an electric potential distribution on a two-dimensional plane parallel to the electrode plate satisfy, the conductivity distribution that satisfies the plurality of relational expressions with respect to the magnetic field information.

With this, a conductivity distribution can be appropriately derived based on the relationship between the magnetic field, the conductivity distribution, and the like. Therefore, it is possible to appropriately inspect for an electrical failure such as a short circuit or the like within a battery.

These general and specific aspects may be implemented using a system, a device, a method, an integrated circuit, a computer program, or a computer-readable, non-transitory recording medium such as a compact disc read-only memory (CD-ROM), or any combination of systems, devices, methods, integrated circuits, computer programs, or recording media.

By using the conductivity distribution derivation method and the conductivity distribution derivation device according to the present invention, it is possible to appropriately derive a conductivity distribution that is effective in inspecting for a short circuit or the like within a battery.

DESCRIPTION OF EMBODIMENTS

Hereinafter, an embodiment and the like are described in detail with reference to the Drawings. Note that each of the embodiment and the like described below shows a general or specific example. The numerical values, shapes, materials, structural elements, the arrangement and connection of the structural elements, steps, the order of the steps etc. shown in the following embodiment and the like are mere examples, and are not intended to limit the scope of the present invention. Furthermore, among the structural elements in the following embodiment and the like, structural elements not recited in any one of the independent claims indicating the broadest concepts of the present invention are described as arbitrary structural elements.

Embodiment

Figure 1:
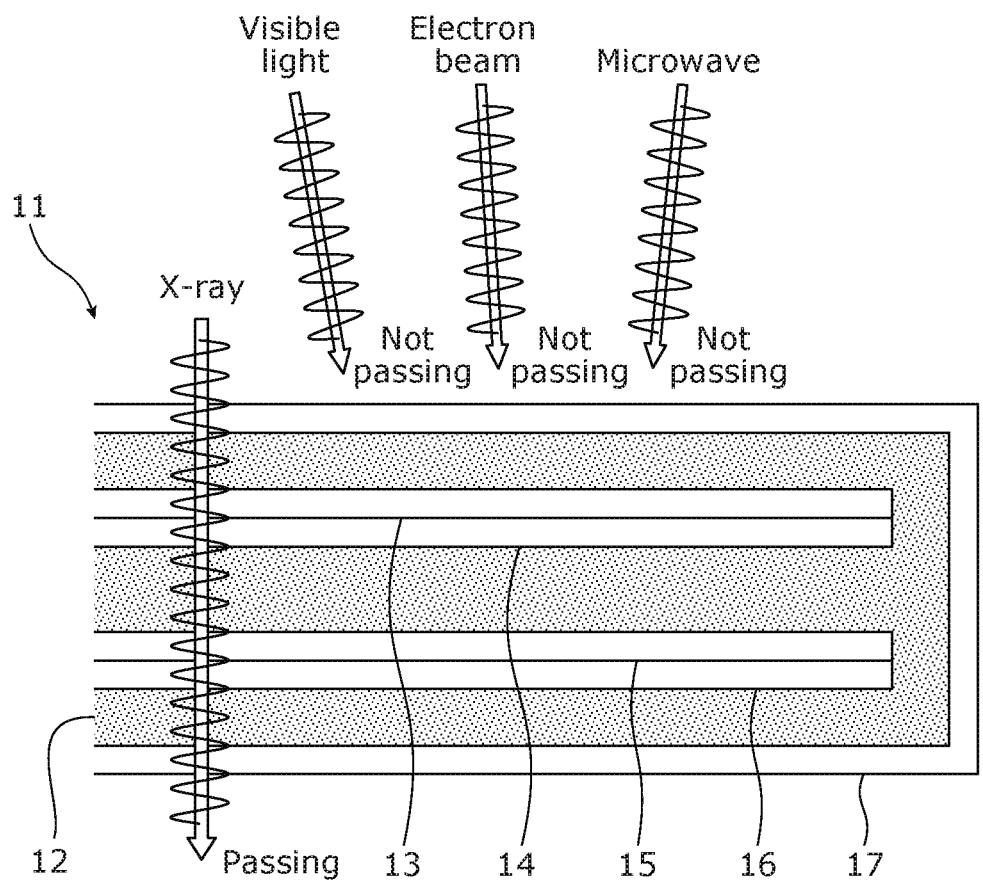
FIG. 1 illustrates a reference example of a battery inspection method.

FIG. 1 illustrates a reference example of a battery inspection method. A battery 11 illustrated in FIG. 1 includes an electrolyte 12, an electric current collector 13, a positive electrode active material 14, a negative electrode active material 15, an electric current collector 16, and a metal package 17. The electrolyte 12, the electric current collector 13, the positive electrode active material 14, the negative electrode active material 15, and the electric current collector 16 are covered with the metal package 17.

Examples of a technical element used in non-destructive inspection include X-ray, visible light, electron beams, microwaves, and ultrasound waves. Among them, visible light, electron beams, and microwaves are not expected to be used for inspecting the battery 11 in a non-destructive manner because the transmittance of visible light, electron beams, and microwaves through the battery 11 is zero. High brightness X-ray can be used for inspecting the battery 11 in a non-destructive manner. For example, it is possible to detect a foreign material in the battery 11 by inspecting the battery 11 with high brightness X-ray in a non-destructive manner.

In the non-destructive inspection with high brightness X-ray, however, it is hard to detect an electrical abnormality of the battery 11. This means that in the non-destructive inspection with high brightness X-ray, it is possible to detect some structural abnormality of the battery 11, but it is hard to recognize what specific electrical abnormality the battery 11 has. A battery inspection system according to the present embodiment therefore uses information on the magnetic field to inspect the battery 11.

Figure 2:
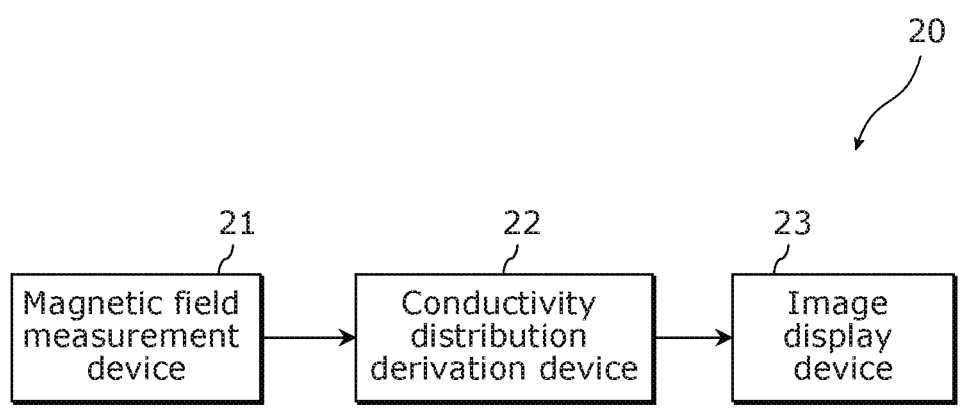
FIG. 2 is a configuration diagram illustrating a battery inspection system according to an embodiment.

FIG. 2 is a configuration diagram illustrating the battery inspection system according to the present embodiment. A battery inspection system 20 illustrated in FIG. 2 includes a magnetic field measurement device 21, a conductivity distribution derivation device 22, and an image display device 23.

The magnetic field measurement device 21 measures the magnetic field and includes, for example, a sensor. Specifically, the magnetic field measurement device 21 measures the magnetic field around the battery 11.

The conductivity distribution derivation device 22 obtains magnetic field information indicating the magnetic field and derives a conductivity distribution within the battery 11 based on the magnetic field information. The conductivity distribution derivation device 22 may be a computer. The conductivity distribution derived by the conductivity distribution derivation device 22 is a conductivity distribution within the battery 11 which is a conductivity distribution on a two-dimensional plane parallel to a flat electrode plate included in the battery 11.

The image display device 23 displays an image and includes a display (a display unit). Specifically, the image display device 23 displays an image representing the conductivity distribution derived by the conductivity distribution derivation device 22. The image which is to be displayed by the image display device 23 may be generated by the image display device 23 or may be generated by the conductivity distribution derivation device 22.

Figure 3:
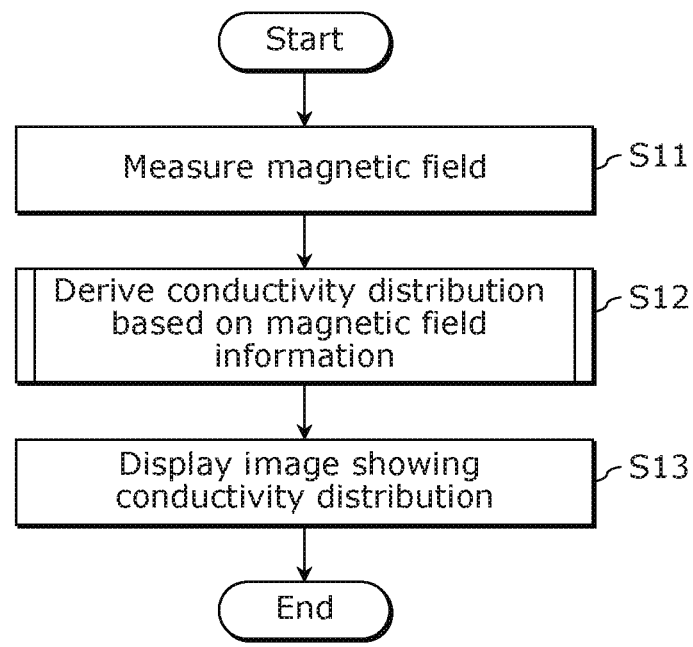
FIG. 3 is a flowchart illustrating an operation of a battery inspection system according to an embodiment.

FIG. 3 is a flowchart illustrating an operation of the battery inspection system 20 illustrated in FIG. 2. First, the magnetic field measurement device 21 measures the magnetic field (S11). Next, the conductivity distribution derivation device 22 derives a conductivity distribution based on the magnetic field information (S12). Next, the image display device 23 displays an image representing the conductivity distribution (S13).

The battery inspection system 20 is capable of displaying the image representing the conductivity distribution within the battery 11 on the basis of the above-described operation. Any electrical abnormality of the battery 11 will be shown in the conductivity distribution. Thus, the battery inspection system 20 is capable of showing an electrical abnormality of the battery 11 by displaying the image representing the conductivity distribution.

A conductivity distribution is information directly indicating an electrical abnormality of the battery 11. The conductivity distribution is very effective in recognizing an electrical abnormality of the battery 11. Next, the conductivity distribution derivation device 22 that derives a conductivity distribution such as that described above is described.

Figure 4:
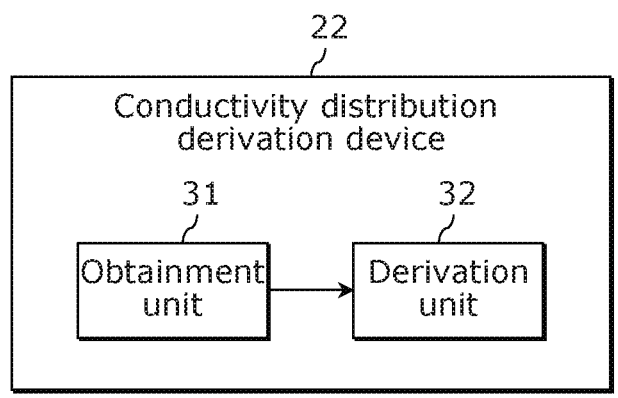
FIG. 4 is a configuration diagram illustrating a conductivity distribution derivation device according to an embodiment.

FIG. 4 is a configuration diagram illustrating the conductivity distribution derivation device 22 illustrated in FIG. 2. For example, the conductivity distribution derivation device 22 includes an obtainment unit 31 and a derivation unit 32 as illustrated in FIG. 4. The conductivity distribution derivation device 22 may further include an analysis unit that analyzes the magnetic field or may further include a generation unit that generates an image representing the conductivity distribution. These structural elements may each be mounted as a dedicated or general-purpose circuit. These may either be mounted as one circuit or may be mounted as two or more circuits.

The obtainment unit 31 obtains magnetic field information indicating the magnetic field. For example, the obtainment unit 31 obtains the magnetic field information from the magnetic field measurement device 21. The obtainment unit 31 may analyze the magnetic field information obtained from the magnetic field measurement device 21, to obtain more detailed magnetic field information.

The derivation unit 32 derives a conductivity distribution within the battery 11 based on the relationship between the magnetic field and the conductivity distribution. More specifically, the derivation unit 32 derives a conductivity distribution based on the relationship between a component of a magnetic field vector in the x-direction, a component of the magnetic field vector in the y direction, the conductivity distribution, and an electric potential distribution. In particular, among components of the magnetic field, components other than a component of the magnetic field vector in the z direction, namely, only the component of the magnetic field vector in the x-direction and the component of the magnetic field vector in the y direction, are used when the derivation unit 32 derives a conductivity distribution.

The x direction and the y direction are two directions parallel to the flat electrode plate included in the battery 11 which are perpendicular to each other. The z direction is perpendicular to the x direction and the y direction. The conductivity distribution is on a two-dimensional plane parallel to the flat electrode plate included in the battery 11. The electric potential distribution is on a two-dimensional plane parallel to the flat electrode plate included in the battery 11.

Note that the component of the magnetic field vector in the x direction, the component of the magnetic field vector in the y direction, and the component of the magnetic field vector in the z direction are also referred to herein as an x component of the magnetic field vector, a y component of the magnetic field vector, and a z component of the magnetic field vector, respectively.

Figure 5:
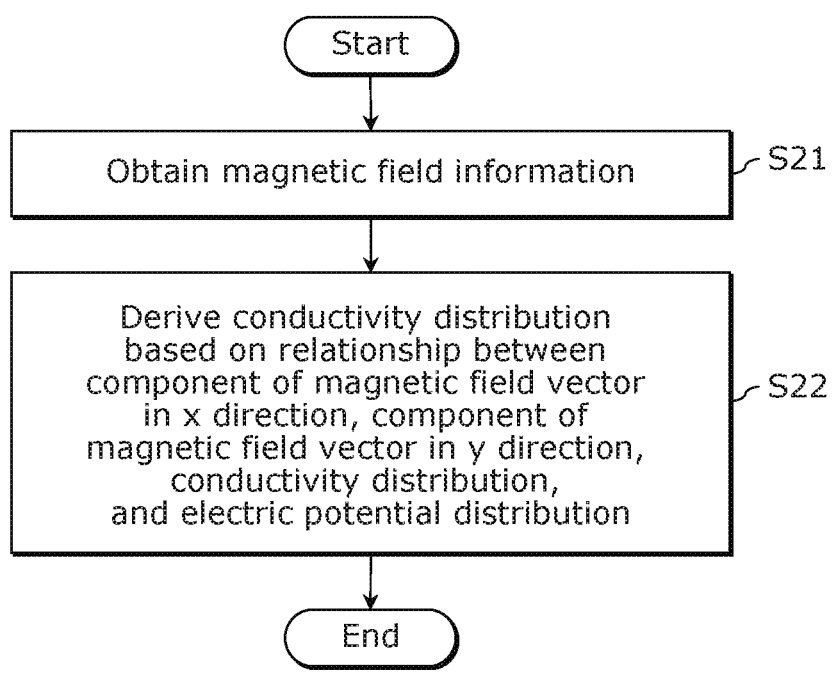
FIG. 5 is a flowchart illustrating an operation of a conductivity distribution derivation device according to an embodiment.

FIG. 5 is a flowchart illustrating an operation of the conductivity distribution derivation device 22 illustrated in FIG. 4. First, the obtainment unit 31 obtains the magnetic field information (S21). Next, the derivation unit 32 derives a conductivity distribution based on the relationship between the component of the magnetic field vector in the x-direction, the component of the magnetic field vector in the y direction, the conductivity distribution, and the electric potential distribution (S22). The conductivity distribution derivation device 22 is capable of deriving a conductivity distribution on the basis of the above-described operation.

Next, the battery inspection system 20 and the conductivity distribution derivation device 22 are described in more detail.

Figure 6:
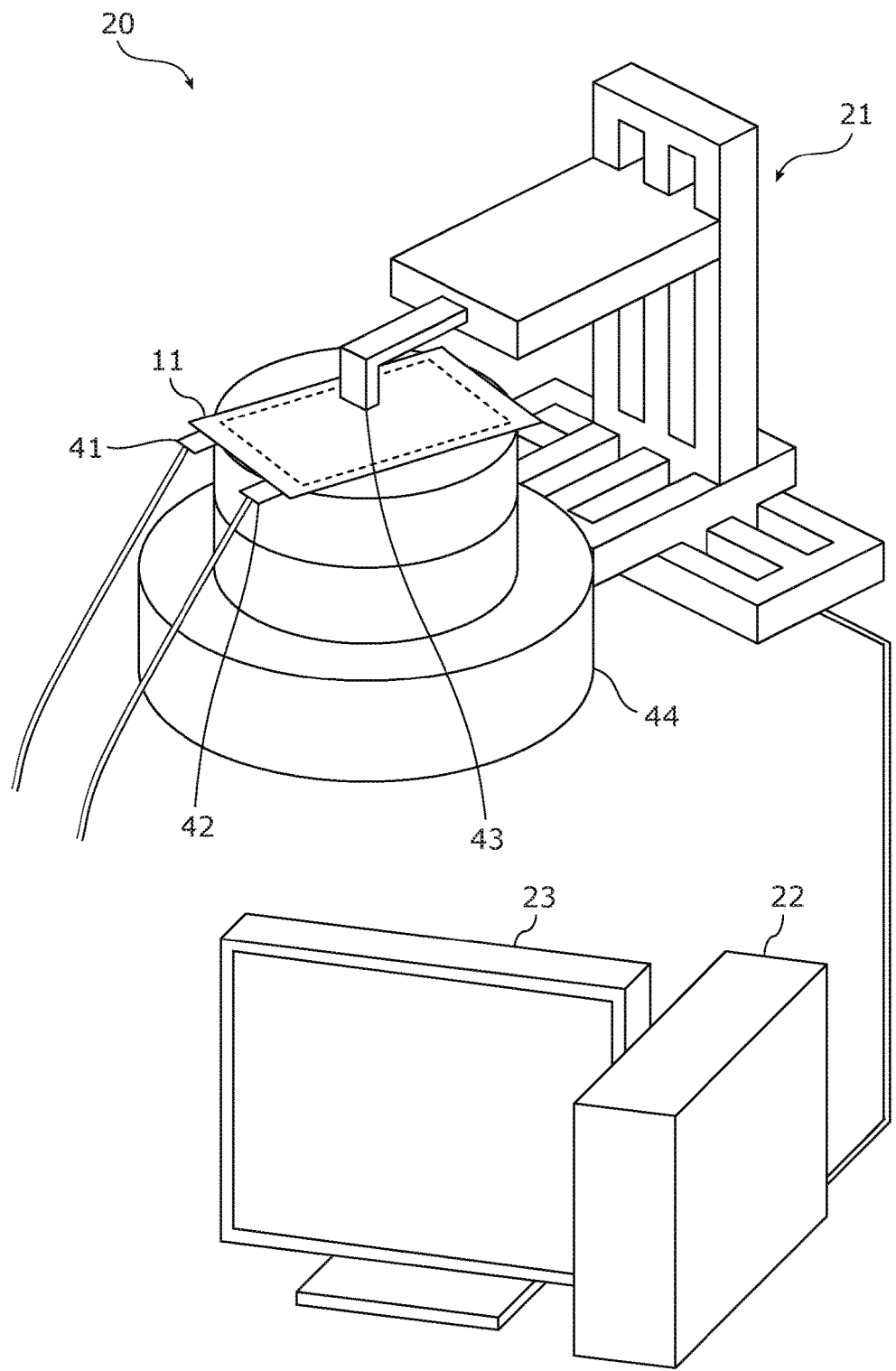
FIG. 6 is a schematic diagram illustrating a battery inspection system according to an embodiment.

FIG. 6 is a schematic diagram illustrating the battery inspection system 20 illustrated in FIG. 2. The battery inspection system 20 illustrated in FIG. 6 includes the magnetic field measurement device 21, the conductivity distribution derivation device 22, and the image display device 23.

The magnetic field measurement device 21 includes a tunneling magneto resistive (TMR) sensor 43 as a magnetic sensor. Note that the TMR sensor 43 is a mere example; a different type of sensor may be used. The magnetic field measurement device 21 includes a slidable structure. With this, the magnetic field measurement device 21 is capable of scanning an area around the battery 11 by using the TMR sensor 43.

Furthermore, the magnetic field measurement device 21 includes a rotating table 44. The rotating table 44 is a base on which an inspection object (the battery 11) is to be placed, and includes a rotatable structure. With this, the magnetic field measurement device 21 is capable of scanning an area around the battery 11 at various angles of rotation.

The conductivity distribution derivation device 22 obtains the magnetic field information and derives a conductivity distribution within the battery 11 based on the magnetic field information. For example, the conductivity distribution derivation device 22 is a computer such as that illustrated in FIG. 6.

The image display device 23 displays an image representing the conductivity distribution. For example, the image display device 23 is a display device having a screen such as that illustrated in FIG. 6.

The battery 11 to be inspected with the battery inspection system 20 is a lithium battery, a lithium-ion battery, or the like. The battery 11 has one pair of flat electrode plates. Furthermore, the battery 11 has one pair of electrode terminals 41 and 42. The magnetic field measurement device 21 measures the magnetic field around the battery 11 while an electric current flows through the electrode terminals 41 and 42 with conductor wires connected thereto.

Figure 7:
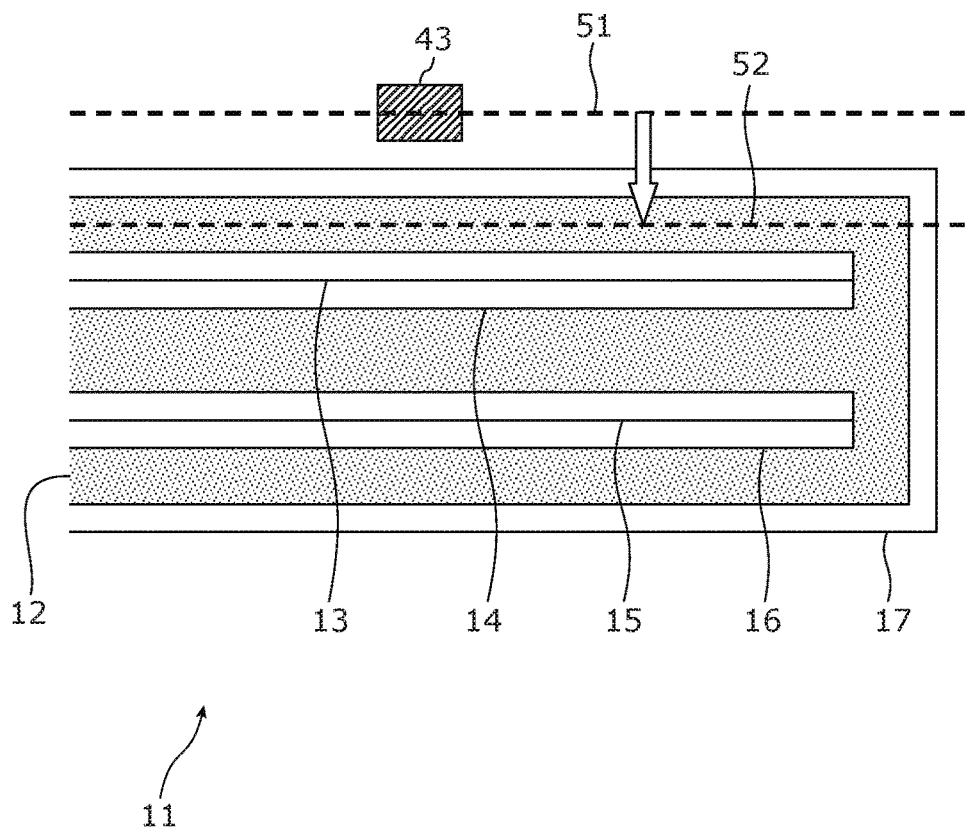
FIG. 7 illustrates a battery being inspected according to an embodiment.

FIG. 7 illustrates the battery 11 illustrated in FIG. 6 being inspected. Similarly to FIG. 1, the battery 11 illustrated in FIG. 7 includes the electrolyte 12, the electric current collector 13, the positive electrode active material 14, the negative electrode active material 15, the electric current collector 16, and the metal package 17. The electrolyte 12, the electric current collector 13, the positive electrode active material 14, the negative electrode active material 15, and the electric current collector 16 are covered with the metal package 17.

With the TMR sensor 43, the magnetic field measurement device 21 measures the magnetic field in a scan target plane 51 above the battery 11 placed on the rotating table 44. The conductivity distribution derivation device 22 may, for example, obtain information on the magnetic field measured in the scan target plane 51 from the magnetic field measurement device 21 and analyze the obtained information to obtain information on the magnetic field in a reconstruction target plane 52. In other words, the conductivity distribution derivation device 22 may obtain information on the magnetic field in the reconstruction target plane 52 based on the information on the magnetic field in the scan target plane 51.

Methods of analyzing information on the magnetic field are described in, for example, International Publication WO2008/123432 (hereinafter, PTL 2) and International Publication WO2012/153496 (hereinafter, PTL 3). Specifically, PTL 2 and PTL 3 describe methods of analyzing information on the magnetic field by solving Maxwell equation.

The conductivity distribution derivation device 22 may use the method described in PTL 2, PTL 3, or the like. Alternatively, the magnetic field measurement device 21 may obtain information on the magnetic field in the reconstruction target plane 52 by using the method described in PTL 2, PTL 3, or the like. In this case, the conductivity distribution derivation device 22 may obtain the information on the magnetic field in the reconstruction target plane 52 from the magnetic field measurement device 21.

The conductivity distribution derivation device 22 may derive a conductivity distribution based on the information on the magnetic field in the scan target plane 51 without obtaining the information on the magnetic field in the reconstruction target plane 52.

Figure 8:
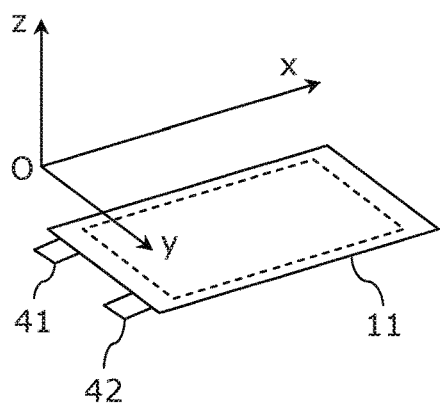
FIG. 8 illustrates a coordinate system according to an embodiment.

FIG. 8 is a coordinate system used by the battery inspection system 20 illustrated in FIG. 6. In FIG. 8, the relationship between the battery 11 illustrated in FIG. 6 and the coordinate system is illustrated. The x direction and the y direction are two directions parallel to the flat electrode plate included in the battery 11 which are perpendicular to each other. The z direction is perpendicular to the x direction and the y direction.

A coordinate in the x direction is also referred to as x or an x-coordinate; a coordinate in the y direction is also referred to as y or a y-coordinate; and a coordinate in the z direction is also referred to as z or a z-coordinate. The x direction corresponds to the x-axis and is also referred to as an x-axis direction. Likewise, the y direction corresponds to the y-axis and is also referred to as a y-axis direction. Likewise, the z direction corresponds to the z-axis and is also referred to as a z-axis direction.

The following describes, on the basis of the coordinate system illustrated in FIG. 8, the relationship between the component of the magnetic field vector in the x-direction, the component of the magnetic field vector in the y direction, the conductivity distribution on a two-dimensional plane parallel to the electrode plate, and the electric potential distribution on a two-dimensional plane parallel to the electrode plate.

Figure 9:
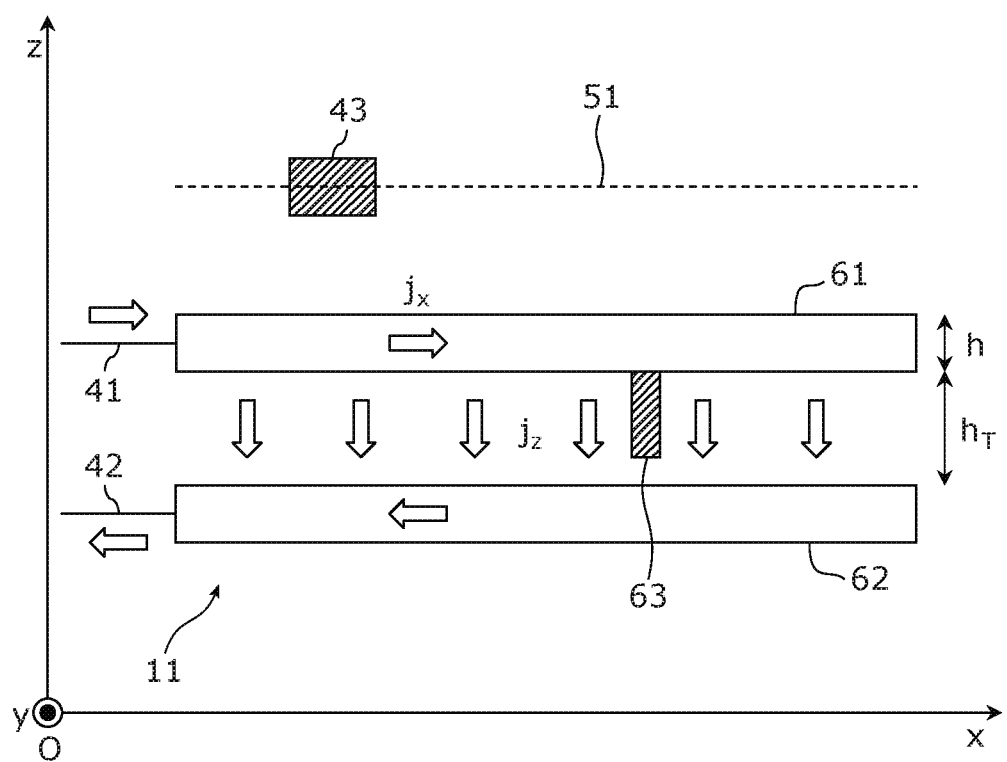
FIG. 9 illustrates the relationship between a magnetic field, an electric potential distribution, and a conductivity distribution that are used by a battery inspection system according to an embodiment.

FIG. 9 illustrates the relationship between the magnetic field, the electric potential distribution, and the conductivity distribution that are used by the battery inspection system 20 illustrated in FIG. 6. The battery 11 corresponds to a single-layer lithium-ion battery cell and has one pair of flat electrode plates 61 and 62. The electrode plate 61 corresponds to the electric current collector 13 and the positive electrode active material 14. The electrode plate 62 corresponds to the negative electrode active material 15 and the electric current collector 16. The electrolyte 12 is present between the one pair of electrode plates 61 and 62.

The thickness of the electrode plate 61 is represented by h, and the distance between the electrode plates 61 and 62 is represented by $h_T$. The electrode plate 61 is connected to the electrode terminal 41, and the electrode plate 62 is connected to the electrode terminal 42. With the TMR sensor 43, the magnetic field measurement device 21 measures the magnetic field in the scan target plane 51 above the battery 11 while an electric current flows through the battery 11.

An electric current is denoted by j. In particular, the electric current in the x direction is noted by $j_x$, the electric current in the y direction is denoted by $j_y$, and the electric current in the z direction is denoted by $j_z$.

The conductivity distribution between the one pair of electrode plates 61 and 62 is normally fixed. When dendrites 63 grow, the conductivity distribution changes. Formation of the dendrites 63 results from metal deposition on the electrode plate 61 or the electrode plate 62. The conductivity of the dendrites 63 is higher than that of the electrolyte. Therefore, the dendrites 63 may cause a short circuit. For this reason, the battery inspection system 20 derives a conductivity distribution and inspects the condition of the battery 11.

The relationship between the magnetic field, the electric potential distribution, and the conductivity distribution is described below with reference to FIG. 9. In the description below, a conductivity distribution $\sigma(x, y)$ indicates the conductivity distribution on a two-dimensional plane between the one pair of electrode plates 61 and 62. The electric potential distribution [Math. 11] indicates an electric potential distribution on a two-dimensional plane at a surface of the electrode plate 61. Conductivity $\sigma_0$ denotes the conductivity of the electrode plate 61. The conductivity $\sigma_0$ is constant at the electrode plate 61 throughout the x-coordinates or the y-coordinates.

[Math. 11]

$$\varphi(x,y)$$

First, the relationship in Expression 1 is formed according to a steady-state Maxwell equation.

[Math. 12]

$$\nabla \times E = -\partial_t B = 0$$

$$\nabla \times H = j + \partial_t D = j \quad \text{Expression 1}$$

In this expression, E denotes an electric field, B denotes magnetic flux density, H denotes a magnetic field, D denotes electric flux density, t denotes time, and $\partial_t$ denotes a partial differential with respect to t. According to the first equation in Expression 1, the electric field E is represented by Expression 2 on the basis of the electric potential.

[Math. 13]

$$E = -\nabla \varphi \quad \text{Expression 2}$$

An electric current j at the electrode plate 61 is represented by Expression 3 based on the electric field E, the conductivity $\sigma_0$, and Expression 2.

[Math. 14]

$$j = \sigma_0 E = -\sigma_0 \nabla \varphi(x,y) \quad \text{Expression 3}$$

In the meantime, Expression 4 is formed according to the second equation in Expression 1.

[Math. 15]

$$\nabla \times \nabla \times H = \nabla(\nabla \cdot H) - \Delta H \quad \text{Expression 4}$$
$$= -\Delta H$$
$$= \nabla \times j$$
$$= \nabla \times (\sigma E)$$

In this expression, $\Delta$ denotes an operator called a Laplace operator or Laplacian. According to Expression 3 and Expression 4, Expression 5 is formed at the surface of the electrode plate 61.

[Math. 16]

$$\Delta H_z = \nabla \times (\sigma_0 \nabla \varphi) = 0 \quad \text{Expression 5}$$

In this expression, $H_z$ denotes a z component of the magnetic field vector. As shown in Expression 5, the electric current flowing through the electrode plate 61 does not lead to generation of the z component $H_z$ of the magnetic field vector. The electric current flowing in parallel with the z direction between the one pair of electrode plates 61 and 62 does not lead to generation of the z component $H_z$ of the magnetic field vector either. This is because the electrode plate 61 of the battery 11, which is different from a printed board having a via hole, has a constant conductivity $\sigma_0$ with no holes or the like. Furthermore, Expression 6 is formed according to a continuity equation for the electric current at the electrode plate 61.

[Math. 17]

$$(\partial_x h_x + \partial_y j_y)h + j_z = 0 \quad \text{Expression 6}$$

In this expression, $\partial_x$ denotes a partial differential with respect to x, and $\partial_y$ denotes a partial differential with respect to y. Expression 6 is represented by Expression 7 using the electric potential distribution [Math. 18].

[Math. 18]

$$\varphi$$

[Math. 19]

$$-h\partial_x(\sigma_0 \nabla_x \varphi) - h\partial_y(\sigma_0 \nabla_y \varphi) + h_T^{-1} \sigma(x,y)\varphi = 0 \quad \text{Expression 7}$$

In this expression, $\nabla_x$ denotes a partial differential with respect to x, and $\nabla_y$ denotes a partial differential with respect to y. Therefore, Expression 7 is represented by Expression 8.

[Math. 20]

$$(\partial_x^2 + \partial_y^2)\varphi = \frac{1}{hh_T\sigma_0}\sigma(x,y)\varphi \quad \text{Expression 8}$$

The electric current in the three-dimensional space is represented by Expression 9 where $z_0$ denotes the z-coordinate of the center of the electrode plate 61.

[Math. 21]

$$j=\{-\sigma_0\nabla_x\varphi(x,y), -\sigma_0\nabla_y\varphi(x,y), -h_T^{-1}\sigma(x,y)\varphi(x,y)\}h\delta(z-z_0) \quad \text{Expression 9}$$

In the expression, $\delta$ denotes a delta function. The relationship between a magnetic field vector H and an electric current vector j is represented by Expression 10 according to Expression 9.

[Math. 22]

$$\begin{aligned}\Delta H &= -\nabla \times j \\ &= -\nabla \times \{-\sigma_0\nabla_x\varphi(x,y), -\sigma_0\nabla_y\varphi(x,y), -h_T^{-1}\sigma(x,y)\varphi(x,y)\}h\delta(z-z_0) \\ &= \begin{bmatrix} e_1 & e_2 & e_3 \\ \partial_x & \partial_y & \partial_z \\ \sigma_0 h\nabla_x\varphi(x,y)\delta(z-z_0) & \sigma_0 h\nabla_y\varphi(x,y)\delta(z-z_0) & h_T^{-1}h\sigma(x,y)\varphi(x,y)\delta(z-z_0) \end{bmatrix} \\ &= \begin{bmatrix} \partial_y\{h_T^{-1}h\sigma(x,y)\varphi(x,y)\delta(z-z_0)\} - \partial_z\{\sigma_0 h\nabla_y\varphi(x,y)\delta(z-z_0)\} \\ -\partial_x\{h_T^{-1}h\sigma(x,y)\varphi(x,y)\delta(z-z_0)\} + \partial_z\{\sigma_0 h\nabla_x\varphi(x,y)\delta(z-z_0)\} \\ \partial_x\{\sigma_0 h\nabla_y\varphi(x,y)\delta(z-z_0)\} - \partial_y\{\sigma_0 h\nabla_x\varphi(x,y)\delta(z-z_0)\} \end{bmatrix}\end{aligned}$$

Expression 10

In the z component, the first term and the second term of the z component match each other. In other words, the z component is 0. This means that the electric current in the battery 11 does not lead to generation of the z component $H_z$ of the magnetic field vector. On the other hand, the x component and the y component are not 0. Therefore, regarding the relationship between the x component $H_x$ of the magnetic field vector, the y component $H_y$ of the magnetic field vector, the conductivity distribution $\sigma$, and the electric potential distribution [Math. 23], a system of equations in Expression 11 is formed according to Expression 8 and Expression 10.

[Math. 23]

$\varphi$

[Math. 24]

$$\Delta H_x = h_T^{-1} h\partial_y\{\sigma(x,y)\varphi(x,y)\}\delta(z-z_0) - \sigma_0 h\{\partial_y\varphi(x,y)\}\delta'(z-z_0)$$

$$\Delta H_y = h_T^{-1} h\partial_x\{\sigma(x,y)\varphi(x,y)\}\delta(z-z_0) - \sigma_0 h\{\partial_x\sigma(x,y)\}\delta'(z-z_0)$$

$$\partial_x^2\varphi + \partial_y^2\varphi = (\sigma_0 h h_T)^{-1}\sigma(x,y)\varphi(x,y) \quad \text{Expression 11}$$

As stated above, Expression 11 is formed regarding the relationship between the x component $H_x$ of the magnetic field vector, the y component $H_y$ of the magnetic field vector, the conductivity distribution $\sigma$, and the electric potential distribution [Math. 25].

$\varphi$ [Math. 25]

The first equation in Expression 11 is a relational expression representing the relationship between the x component $H_x$ of the magnetic field vector, the conductivity distribution $\sigma$, and the electric potential distribution [Math. 26].

$\varphi$ [Math. 26]

The second equation in Expression 11 is a relational expression representing the relationship between the y component $H_y$ of the magnetic field vector, the conductivity distribution $\sigma$, and the electric potential distribution [Math. 27].

$\varphi$ [Math. 27]

The third equation in Expression 11 is a relational expression representing the relationship between the conductivity distribution $\sigma$ and the electric potential distribution [Math. 28].

$\varphi$ [Math. 28]

This means that Expression 11 is a relational expression (a plurality of relational expressions) which the x component $H_x$ of the magnetic field vector, the y component $H_y$ of the magnetic field vector, the conductivity distribution $\sigma$, and the electric potential distribution [Math. 29] satisfy.

$\varphi$ [Math. 29]

The first equation in Expression 11 is a relational expression which the x component $H_x$ of the magnetic field vector, the conductivity distribution $\sigma$, and the electric potential distribution [Math. 30] satisfy.

$\varphi$ [Math. 30]

The second equation in Expression 11 is a relational expression which the y component $H_y$ of the magnetic field vector, the conductivity distribution $\sigma$, and the electric potential distribution [Math. 31] satisfy.

$\varphi$ [Math. 31]

The third equation in Expression 11 is a relational expression which the conductivity distribution $\sigma$ and the electric potential distribution [Math. 32] satisfy.

$\varphi$ [Math. 32]

It is possible to specify the x component $H_x$ of the magnetic field vector and the y component $H_y$ of the magnetic field vector from the magnetic field information. In addition, the conductivity distribution $\sigma$ and the electric potential distribution [Math. 33] which satisfy Expression 11 can be specified on the basis of the x component $H_x$ of the magnetic field vector and the y component $H_y$ of the magnetic field vector.

$\varphi$ [Math. 33]

The derivation unit 32 of the conductivity distribution derivation device 22 derives a conductivity distribution $\sigma$ from the magnetic field information according to Expression 11 representing the relationship between the x component $H_x$ of the magnetic field vector, the y component $H_y$ of the magnetic field vector, the conductivity distribution σ, and the electric potential distribution [Math. 34].

$$\varphi \qquad \text{[Math. 34]}$$

With this, the conductivity distribution derivation device 22 is capable of appropriately deriving the conductivity distribution σ. It is then possible to appropriately inspect for an electrical failure with reference to the derived conductivity distribution σ.

Herein, wording to the effect of deriving the conductivity distribution σ according to Expression 11 may include the meaning of deriving the conductivity distribution σ according to an expression that is substantially the same as Expression 11. For example, the expression that is substantially the same as Expression 11 may be an expression obtained by deforming Expression 11 or may be an expression similar to Expression 11.

Furthermore, the conductivity distribution derivation device 22 may derive the conductivity distribution σ according to a relational expression representing the relationship between the x component $H_x$ of the magnetic field vector, the y component $H_y$ of the magnetic field vector, the conductivity distribution σ, and the electric potential distribution [Math. 35], which is different from Expression 11.

$$\varphi \qquad \text{[Math. 35]}$$

For example, such a relational expression can be derived on the basis of various laws of physics.

Furthermore, there are a plurality of extended examples that can be arbitrarily applied to the present embodiment. These extended examples are described below.

Extended Example 1

First, Extended example 1 is described. In Extended example 1, the derivation unit 32 of the conductivity distribution derivation device 22 determines a model for the conductivity distribution σ and a model for the electric potential distribution [Math. 36], and derives the x component $H_x$ of the magnetic field vector and the y component $H_y$ of the magnetic field vector on the basis of the model for the conductivity distribution σ and the model for the electric potential distribution [Math. 37].

$$\varphi \qquad \text{[Math. 36]}$$

$$\varphi \qquad \text{[Math. 37]}$$

The mode is also referred to as a candidate. When the derived x component $H_x$ and y component $H_y$ fit the magnetic field information obtained through the magnetic field measurement device 21 or the like, the derivation unit 32 determines a model for the conductivity distribution σ and a model for the electric potential distribution [Math. 38] as the conductivity distribution σ and the electric potential distribution [Math. 39].

$$\varphi \qquad \text{[Math. 38]}$$

$$\varphi \qquad \text{[Math. 39]}$$

More specifically, first, the derivation unit 32 determines a model for the conductivity distribution σ and a model for the electric potential distribution [Math. 41] so that a model for the conductivity distribution σ and a model for the electric potential distribution [Math. 40] satisfy the third equation in Expression 11.

$$\varphi \qquad \text{[Math. 40]}$$

$$\varphi \qquad \text{[Math. 41]}$$

The model determined first is also referred to as an initial model. The initial model may be determined in advance or may be determined in accordance with input from a user of the battery inspection system 20. In addition, the initial model may be determined by the properties of the battery 11.

Furthermore, the derivation unit 32 may first determine a model for the conductivity distribution σ and then determine a model for the electric potential distribution [Math. 42] according to the third equation in Expression 11.

$$\varphi \qquad \text{[Math. 42]}$$

Alternatively, the derivation unit 32 may first determine a model for the electric potential distribution [Math. 43] and then determine a model for the conductivity distribution σ according to the third equation in Expression 11.

$$\varphi \qquad \text{[Math. 43]}$$

Next, the derivation unit 32 derives the x component $H_x$ of the magnetic field vector based on the model for the conductivity distribution σ, the model for the electric potential distribution [Math. 44], and the first equation in Equation 11.

$$\varphi \qquad \text{[Math. 44]}$$

Furthermore, the derivation unit 32 derives the y component $H_y$ of the magnetic field vector based on the model for the conductivity distribution σ, the model for the electric potential distribution [Math. 45], and the second equation in Equation 11.

$$\varphi \qquad \text{[Math. 45]}$$

When the derived x component $H_x$ and y component $H_y$ fit the magnetic field information obtained by the obtainment unit 31, the derivation unit 32 determines the model for the conductivity distribution σ as the conductivity distribution σ. Furthermore, the derivation unit 32 determines the model for the electric potential distribution [Math. 46] in this case as the electric potential distribution [Math. 47].

$$\varphi \qquad \text{[Math. 46]}$$

$$\varphi \qquad \text{[Math. 47]}$$

The derived x component $H_x$ and y component $H_y$ do not fit the magnetic field information obtained by the obtainment unit 31, the derivation unit 32 determines a new model for the conductivity distribution σ and a new model for the electric potential distribution [Math. 48]. The derivation unit 32 may determine these new models based on a difference between the derived x component $H_x$ and the x component $H_x$ of the magnetic field vector indicated by the magnetic field information and a difference between the derived y component $H_y$ and the y component $H_y$ of the magnetic field vector indicated by the magnetic field information.

$$\varphi \qquad \text{[Math. 48]}$$

The derivation unit 32 derives the x component $H_x$ of the magnetic field vector and the y component $H_y$ of the magnetic field vector on the basis of the newly determined model. When the derived x component $H_x$ and y component $H_y$ fit the magnetic field information, the derivation unit 32 determines these models as the conductivity distribution σ and the electric potential distribution [Math. 49].

$$\varphi \qquad \text{[Math. 49]}$$

When the derived x component $H_x$ and y component $H_y$ do not fit the magnetic field information, the derivation unit 32 determines new models again.

The derivation unit 32 repeats the above-described procedures to search for models with which the x component $H_x$ and the y component $H_y$ that fit the magnetic field information are derived. Specifically, the derivation unit 32 changes models, derives the x component $H_x$ of the magnetic field vector and the y component $H_y$ of the magnetic field vector by using each of the models, and determines, as the conductivity distribution σ and the electric potential distribution [Math. 50], the models with which the derived x component $H_x$ and y component $H_y$ fit the magnetic field vector information. In such a process, a plurality of models are also searched for an appropriate model.

[Math. 50]

$$\varphi$$

The derivation unit 32 may search for an appropriate model by performing parallel processing on a plurality of models. For example, in this case, the derivation unit 32 derives in parallel a plurality of magnetic fields corresponding to the plurality of models. The derivation unit 32 then identifies a magnetic field that fits the magnetic field information from the plurality of magnetic fields, and identifies a model used to derive the identified magnetic field. This allows the derivation unit 32 to retrieve an appropriate model in a short period of time.

The derivation unit 32 may perform such parallel processing by using a general purpose graphics processing unit (GPGPU). The GPGPU is an approach for using an image processing device (an image processing unit) in an application different from image processing. The GPGPU is suitable for parallel processing or a repeating process. Therefore, the derivation unit 32 is capable of retrieving an appropriate model in a shorter period of time by using the GPGPU.

The derivation unit 32 or the conductivity distribution derivation device 22 may include an image processing device that can be used for the GPGPU. Such an image processing device may be a device for GPGPU.

According to Extended example 1, the conductivity distribution derivation device 22 is capable of deriving a conductivity distribution that fits the relational expression through the repetition of the same or similar computation. Furthermore, the conductivity distribution derivation device 22 is capable of deriving the conductivity distribution σ by using the GPGPU which is capable of the same or similar computation at high speed.

Extended Example 2

Next, Extended example 2 is described. In Extended example 2, the derivation unit 32 of the conductivity distribution derivation device 22 derives the conductivity distribution σ according to a relational expression that allows the conductivity distribution σ to be derived directly from the magnetic field information. The relational expression that allows the conductivity distribution σ to be derived directly from the magnetic field information is derived from Expression 11. The following describes in detail the relational expression that is derived from Expression 11.

First, Expression 12 is derived by substituting [Math. 51] of the third equation in Expression 11 into the first terms on the right side of the first equation and the second equation in Expression 11.

[Math. 51]

$$\sigma(x,y)\varphi(x,y)$$

[Math. 52]

$$\Delta H_x = h^2 \sigma_0 \partial_y \{\partial_x^2 \varphi + \partial_y^2 \varphi\} \delta(z-z_0) - \sigma_0 h \{\partial_y \varphi(x,y)\} \delta'(z-z_0)$$

$$\Delta H_y = h^2 \sigma_0 \partial_x \{\partial_x^2 \varphi + \partial_y^2 \varphi\} \delta(z-z_0) - \sigma_0 h \{\partial_x \varphi(x,y)\} \delta'(z-z_0)$$

Expression 12

Next, Expression 14 is derived by the Fourier transform of Expression 12 with respect to the x direction and the y direction and by using the symbols defined in Expression 13. Note that the first equation in Expression 13 represents a Fourier-transformed image of the electric potential distribution [Math. 53] obtained through a Fourier-transform with respect to the x direction and the y direction.

[Math. 53]

$$\varphi$$

The second equation in Expression 13 represents a Fourier-transformed image of the x component $H_x$ of the magnetic field vector obtained through a Fourier-transform with respect to the x direction and the y direction. The third equation in Expression 13 represents a Fourier-transformed image of the y component $H_y$ of the magnetic field vector obtained through a Fourier-transform with respect to the x direction and the y direction.

[Math. 54]

$$\tilde{\varphi}(k_x, k_y) = \int_{-\infty}^{\infty}\int_{-\infty}^{\infty} e^{-ik_x x - ik_y y} \varphi(x, y) dx dy$$

$$Q_x(k_x, k_y, z) = \int_{-\infty}^{\infty}\int_{-\infty}^{\infty} e^{-ik_x x - ik_y y} H_x(x, y, z) dx dy$$

$$Q_y(k_x, k_y, z) = \int_{-\infty}^{\infty}\int_{-\infty}^{\infty} e^{-ik_x x - ik_y y} H_y(x, y, z) dx dy$$

Expression 13

[Math. 55]

$$\frac{d^2}{dz^2}Q_x - (k_x^2 + k_y^2)Q_x =$$
$$-h^2\sigma_0(ik_y)(k_x^2 + k_y^2)\tilde{\varphi}\delta(z-z_0) - \sigma_0 h(ik_y)\tilde{\varphi}\delta'(z-z_0)$$

$$\frac{d^2}{dz^2}Q_y - (k_x^2 + k_y^2)Q_y =$$
$$h^2\sigma_0(ik_x)(k_x^2 + k_y^2)\tilde{\varphi}\delta(z-z_0) + \sigma_0 h(ik_x)\tilde{\varphi}\delta'(z-z_0)$$

Expression 14

The particular solutions for $Q_x$ and $Q_y$ of Expression 14 are represented by Expression 16 using a Green's function $G_0(z, z_0, k)$ defined in Expression 15.

[Math. 56]

$$G_0(z, z_0, k) = \frac{1}{2k} e^{-k|z-z_0|}$$

$$k = \sqrt{k_x^2 + k_y^2}$$

$$\frac{\partial^2}{\partial z^2} G_0(z, z_0, k) - k^2 G_0(z, z_0, k) = \delta(z-z_0)$$

Expression 15

[Math. 57]

$$Q_x(k_x, k_y, z) =$$
$$\left\{-h^2\sigma_0(ik_y k^2)G_0(z, z_0, k) - \sigma_0 h(ik_y)\frac{d}{dz}G_0(z, z_0, k)\right\}$$
$$\tilde{\varphi}(k_x, k_y)$$

$$Q_y(k_x, k_y, z) =$$
$$\left\{h^2\sigma_0(ik_x k^2)G_0(z, z_0, k) + \sigma_0 h(ik_x)\frac{d}{dz}G_0(z, z_0, k)\right\}$$
$$\tilde{\varphi}(k_x, k_y)$$

Expression 16

A limit of Expression 16 obtained when z approaches $z_0$ is derived using properties represented in Expression 17 below, and thus Expression 18 is obtained.

[Math. 58]

$$\lim_{z \to z_0+0} G_0(z, z_0, k) = \frac{1}{2k}$$

$$\lim_{z \to z_0+0} \frac{d}{dz} G_0(z, z_0, k) = -\frac{1}{2}$$

Expression 17

[Math. 59]

$$Q_x(k_x, k_y, z_0) = \frac{1}{2}\{-h^2\sigma_0(ik_y k) + \sigma_0 h(ik_y)\}\tilde{\varphi}(k_x, k_y)$$

$$Q_y(k_x, k_y, z_0) = \frac{1}{2}\{-h^2\sigma_0(ik_x k) - \sigma_0 h(ik_x)\}\tilde{\varphi}(k_x, k_y)$$

Expression 18

Expression 19 is derived by combining the first equation and the second equation in Expression 18.

[Math. 60]

$$ik_y Q_x(k_x, k_y, z_0) - ik_x Q_y(k_x, k_y, z_0) = \frac{1}{2} hk^2 \sigma_0(hk-1)\tilde{\varphi}(k_x, k_y)$$

Expression 19

Expression 20 representing a Fourier-transformed image of the electric potential distribution [Math. 61] is obtained according to Expression 19.

$\varphi$ [Math. 61]

[Math. 62]

$$\tilde{\varphi}(k_x, k_y) = \frac{2\{ik_y Q_x(k_x, k_y, z_0) - ik_x Q_y(k_x, k_y, z_0)\}}{hk^2 \sigma_0(hk-1)}$$

Expression 20

Expression 20 is a relational expression derived from the first equation, the second equation, and the third equation in Expression 11 in the above-described procedure; Expression 20 is a relational expression that is based on the first equation, the second equation, and the third equation in Expression 11. The electric potential distribution [Math. 63] is derived by the inverse Fourier transform of Expression 20.

$\varphi$ [Math. 63]

The relational expression that allows the conductivity distribution σ to be derived from the electric potential distribution [Math. 64] is given as in Expression 21 according to the third equation in Expression 11.

$\varphi$ [Math. 64]

[Math. 65]

$$\sigma(x, y) = hh_T\sigma_0 \frac{(\partial_x^2 + \partial_y^2)\varphi}{\varphi}$$

Expression 21

Thus, the derivation unit 32 of the conductivity distribution derivation device 22 is capable of deriving the conductivity distribution σ directly from the magnetic field information according to Expression 20 and Expression 21. Specifically, the derivation unit is capable of deriving the conductivity distribution σ by substituting the magnetic field information into a predetermined analytical expression without repetition of the same or similar computation.

In Expression 20, $Q_x(k_x, k_y, z_0)$ and $Q_y(k_x, k_y, z_0)$ correspond to the magnetic field information on the inside of the battery 11. The following describes an analytical expression that uses $Q_x(k_x, k_y, z_1)$ and $Q_y(k_x, k_y, z_1)$ corresponding to magnetic field information in a scan target plane outside the battery 11. Here, $z_1$ is a z-coordinate in the scan target plane greater than $z_0$.

First, Expression 22 is formed where $z > z_0$ according to Expression 14. Specifically, Expression 22 is formed in a region where z is greater than $z_0$.

[Math. 66]

$$\frac{d^2}{dz^2}Q_x - (k_x^2 + k_y^2)Q_x = 0$$

$$\frac{d^2}{dz^2}Q_y - (k_x^2 + k_y^2)Q_y = 0$$

Expression 22

The general solutions for $Q_x$ and $Q_y$ of the equations in Expression 22 are represented by Expression 23.

[Math. 67]

$$Q_x(k_x, k_y, z) = a_1(k_x, k_y)e^{-(z-z_0)\sqrt{k_x^2+k_y^2}} + b_1(k_x, k_y)e^{(z-z_0)\sqrt{k_x^2+k_y^2}}$$

$$Q_y(k_x, k_y, z) = a_2(k_x, k_y)e^{-(z-z_0)\sqrt{k_x^2+k_y^2}} + b_2(k_x, k_y)e^{(z-z_0)\sqrt{k_x^2+k_y^2}}$$

Expression 23

Thus, the algebraic equations in Expression 24 are formed where $z = z_1$ ($z_1 > z_0$).

[Math. 68]

$$Q_x(k_x, k_y, z_1) = a_1(k_x, k_y)e^{-(z_1-z_0)\sqrt{k_x^2+k_y^2}} + b_1(k_x, k_y)e^{(z_1-z_0)\sqrt{k_x^2+k_y^2}}$$

$$\partial_z Q_x(k_x, k_y, z_1) = \sqrt{k_x^2 + k_y^2}\{-a_1(k_x, k_y)e^{-(z_1-z_0)\sqrt{k_x^2+k_y^2}} + b_1(k_x, k_y)e^{(z_1-z_0)\sqrt{k_x^2+k_y^2}}\}$$

$$Q_y(k_x, k_y, z_1) = a_2(k_x, k_y)e^{-(z_1-z_0)\sqrt{k_x^2+k_y^2}} + b_2(k_x, k_y)e^{(z_1-z_0)\sqrt{k_x^2+k_y^2}}$$

$$\partial_z Q_y(k_x, k_y, z_1) = \sqrt{k_x^2 + k_y^2}\{-a_2(k_x, k_y)e^{-(z_1-z_0)\sqrt{k_x^2+k_y^2}} + b_2(k_x, k_y)e^{(z_1-z_0)\sqrt{k_x^2+k_y^2}}\}$$

Expression 24

Expression 25 is derived by solving the algebraic equations in Expression 24 for $a_1$, $b_1$, $a_2$, and $b_2$.

[Math. 69]

$$a_1(k_x, k_y) = \frac{1}{2}\left\{Q_x(k_x, k_y, z_1) - \frac{1}{\sqrt{k_x^2 + k_y^2}}\partial_z Q_x(k_x, k_y, z_1)\right\} e^{(z_1-z_0)\sqrt{k_x^2+k_y^2}}$$

$$b_1(k_x, k_y) = \frac{1}{2}\left\{Q_x(k_x, k_y, z_1) + \frac{1}{\sqrt{k_x^2 + k_y^2}}\partial_z Q_x(k_x, k_y, z_1)\right\} e^{-(z_1-z_0)\sqrt{k_x^2+k_y^2}}$$

$$a_2(k_x, k_y) = \frac{1}{2}\left\{Q_y(k_x, k_y, z_1) - \frac{1}{\sqrt{k_x^2 + k_y^2}}\partial_z Q_y(k_x, k_y, z_1)\right\} e^{(z_1-z_0)\sqrt{k_x^2+k_y^2}}$$

$$b_2(k_x, k_y) = \frac{1}{2}\left\{Q_y(k_x, k_y, z_1) + \frac{1}{\sqrt{k_x^2 + k_y^2}}\partial_z Q_y(k_x, k_y, z_1)\right\} e^{-(z_1-z_0)\sqrt{k_x^2+k_y^2}}$$

Expression 25

Expression 26 with noise removed is obtained by setting b1 and b2 in Expression 23 to 0 in conformity with Expression 15 and Expression 16.

[Math. 70]

$$Q_x(k_x, k_y, z_0) = a_1(k_x, k_y)$$

$$Q_y(k_x, k_y, z_0) = a_2(k_x, k_y)$$

Expression 26

Expression 27 is obtained according to Expression 25 and Expression 26. Specifically, $Q_x(k_x, k_y, z_0)$ and $Q_y(k_x, k_y, z_0)$ which represent information on the magnetic field inside the battery 11 are represented by Expression 27 by using $Q_x(k_x, k_y, z_1)$ and $Q_y(k_x, k_y, z_1)$ which represent information on the magnetic field outside the battery 11.

[Math. 71]

$$Q_x(k_x, k_y, z_0) = \frac{1}{2}\left\{Q_x(k_x, k_y, z_1) - \frac{1}{\sqrt{k_x^2 + k_y^2}}\partial_z Q_x(k_x, k_y, z_1)\right\} e^{(z_1-z_0)\sqrt{k_x^2+k_y^2}}$$

$$Q_y(k_x, k_y, z_0) = \frac{1}{2}\left\{Q_y(k_x, k_y, z_1) - \frac{1}{\sqrt{k_x^2 + k_y^2}}\partial_z Q_y(k_x, k_y, z_1)\right\} e^{(z_1-z_0)\sqrt{k_x^2+k_y^2}}$$

Expression 27

Thus, the derivation unit 32 of the conductivity distribution derivation device 22 is capable of deriving the conductivity distribution σ directly from the magnetic field information on the outside of the battery 11 according to Expression 20, Expression 21, and Expression 27. Specifically, the derivation unit 32 is capable of deriving the conductivity distribution σ by substituting the magnetic field information on the outside of the battery 11 into a predetermined analytical expression without repetition of the same or similar computation.

Although the battery inspection system and the conductivity distribution derivation device according to the present invention are described thus far based on the embodiment and the like, the present invention is not limited to such an embodiment. Embodiments resulting from various modifications of the embodiment and the like that may be conceived by a person having ordinary skill in the art as well as other embodiments resulting from arbitrary combinations of structural elements of the embodiment and the like are intended to be included within the scope of the present invention.

For example, processes executed by a specific processing unit may be performed by a different processing unit. Furthermore, the order in which processes are performed may be changed, or a plurality of processes may be performed in parallel. The battery to be inspected may be a secondary battery and may also be a primary battery.

The present invention can be implemented, not only as the battery inspection system and the conductivity distribution derivation device, but also as a method having, as steps, the processing units included in the battery inspection system and the conductivity distribution derivation device. For example, such steps are executed by a computer. Moreover, the present invention can be implemented as a program for causing a computer to execute the steps included in the method. In addition, the present invention can be implemented as a non-transitory, computer-readable recording medium, such as a CD-ROM, on which such a program is recorded.

For example, when the present invention is implemented as a program (software), the respective functions according to the present invention may be implemented by executing the program using hardware such as a central processing unit (CPU), memory, and an input and output circuit of the computer. In other words, the CPU obtains, from the memory, the input and output circuit, or the like, data to be processed, computes the data, and outputs the computed result to the memory, the input and output circuit, or the like so that the respective functions are implemented.

Moreover, structural elements included in the battery inspection system or the conductivity distribution derivation device may be implemented as large scale integration (LSI), which is an integrated circuit. These structural elements may be integrated into individual chips, or a portion or all of the structural elements may be integrated into one chip. This kind of integration is referred to as LSI, but, depending on the number of elements per chip, may also be referred to as an integrated circuit (IC), system LSI, super LSI, or ultra LSI.

Moreover, the method of circuit integration is not limited to LSI. Integration may be realized with a specialized circuit or a general purpose processor. A field programmable gate array (FPGA) or a reconfigurable processor that allows reconfiguration of the connection or configuration of the inner circuit cells of the LSI circuit can be used for the same purpose.

Furthermore, when advancement in semiconductor technology and derivatives of other technologies brings forth a circuit integration technology which replaces LSI, it will be appreciated that such a circuit integration technology may be used to integrate the structural elements included in the battery inspection system or the conductivity distribution derivation device.

INDUSTRIAL APPLICABILITY

The conductivity distribution derivation method and the conductivity distribution derivation device according to the present invention can be applied to inspection for a short circuit or the like within a battery, and are applicable to a battery inspection system for inspecting for an electrical failure within a battery, for example.

REFERENCE SIGNS LIST

11 battery
12 electrolyte
13, 16 electric current collector
14 positive electrode active material
15 negative electrode active material
17 metal package
20 battery inspection system
21 magnetic field measurement device
22 conductivity distribution derivation device
23 image display device
31 obtainment unit
32 derivation unit
41, 42 electrode terminal
43 tunneling magneto resistive (TMR) sensor
44 rotating table
51 scan target plane
52 reconstruction target plane
61, 62 electrode plate
63 dendrite

The invention claimed is:

1. A conductivity distribution derivation method for deriving a conductivity distribution within a battery having an electrode plate that is flat, the method comprising:

causing an electric current to flow through a pair of electrode terminals of the battery;

while the electric current flows through the pair of electrode terminals of the battery, obtaining magnetic field information indicating a magnetic field around the battery;

based on a plurality of relational expressions representing a relationship of (i) an x component of a magnetic field vector in an x direction parallel to the electrode plate, (ii) a y component of the magnetic field vector in a y direction parallel to the electrode plate and perpendicular to the x direction, (iii) the conductivity distribution on a two-dimensional plane parallel to the electrode plate, and (iv) an electric potential distribution on a two-dimensional plane parallel to the electrode plate, deriving the conductivity distribution that satisfies the plurality of relational expressions with respect to the magnetic field information; and displaying an image representing the conductivity distribution, the image representing the conductivity distribution indicating an electrical abnormality of the battery, wherein the plurality of relational expressions include a first relational expression, a second relational expression, and a third relational expression, and in the deriving, the conductivity distribution that is represented using σ is derived based on the first relational expression that is represented by [Math. 2], the second relational expression that is represented by [Math. 3], and the third relational expression that is represented by [Math. 4], $$\varphi \qquad \text{[Math. 1]}$$

$$\Delta H_x = h_T^{-1} h \partial_y \{\sigma(x,y)\varphi(x,y)\}\delta(z-z_0) - \sigma_0 h\{\partial_y \varphi(x,y)\}\delta'(z-z_0) \qquad \text{[Math. 2]}$$

$$\Delta H_y = -h_T^{-1} h \partial_x \{\sigma(x,y)\varphi(x,y)\}\delta(z-z_0) - \sigma_0 h\{\partial_y \varphi(x,y)\}\delta'(z-z_0) \qquad \text{[Math. 3]}$$

$$\partial_x^2 \varphi + \partial_y^2 \varphi = (\sigma_0 h h_T)^{-1} \sigma(x,y)\varphi(x,y) \qquad \text{[Math. 4]}$$

where x denotes a coordinate in the x direction, y denotes a coordinate in the y direction, z denotes a coordinate in a z direction perpendicular to the x direction and the y direction, $z_0$ denotes a coordinate of the electrode plate in the z direction, $H_x$ denotes the x component of the magnetic field vector, $H_y$ denotes the y component of the magnetic field vector, h denotes a thickness of the electrode plate in the z direction, $h_T$ denotes a distance between one pair of electrode plates including the electrode plate, $\sigma_0$ denotes conductivity of the electrode plate, σ denotes the conductivity distribution, [Math. 1] denotes the electric potential distribution, δ denotes a delta function, δ' denotes a differential of the delta function, $\partial_x$ denotes a partial differential with respect to x, and $\partial_y$ denotes a partial differential with respect to y.

2. The conductivity distribution derivation method according to claim 1, wherein in the deriving, the conductivity distribution is derived based on a fourth relational expression represented by [Math. 7] and a fifth relational expression represented by [Math. 8], the fourth relational expression being based on the first relational expression, the second relational expression, and the third relational expression, the fifth relational expression being based on the third relational expression,

[Math. 5]

$$\varphi$$

[Math. 6]

$$\tilde{\varphi}$$

[Math. 7]

$$\tilde{\varphi}(k_x, k_y) = \frac{2\{ik_y Q_x(k_x, k_y, z_0) - ik_x Q_y(k_x, k_y, z_0)\}}{hk^2 \sigma_0(hk-1)}$$

[Math. 8]

$$\sigma(x, y) = hh_T \sigma_0 \frac{(\partial_x^2 + \partial_y^2)\varphi}{\varphi}$$

where $k_x$ denotes a wave number in the x direction, $k_y$ denotes a wave number in the y direction, $Q_x$ denotes a function of $H_x$ obtained through a Fourier transform with respect to the x direction and the y direction, $Q_y$ denotes a function of $H_y$ obtained through a Fourier transform with respect to the x direction and the y direction, and [Math. 6] denotes a function of [Math. 5] obtained through a Fourier transform with respect to the x direction and the y direction.

3. The conductivity distribution derivation method according to claim 2, wherein in the deriving, the conductivity distribution is derived based on the fourth relational expression, the fifth relational expression, a sixth relational expression represented by [Math. 9], and a seventh relational expression represented by [Math. 10],

[Math. 9]
$$Q_x(k_x, k_y, z_0) = \frac{1}{2}\left\{Q_x(k_x, k_y, z_1) - \frac{1}{\sqrt{k_x^2+k_y^2}}\partial_z Q_x(k_x, k_y, z_1)\right\}e^{(z_1-z_0)\sqrt{k_x^2+k_y^2}}$$

[Math. 10]
$$Q_y(k_x, k_y, z_0) = \frac{1}{2}\left\{Q_y(k_x, k_y, z_1) - \frac{1}{\sqrt{k_x^2+k_y^2}}\partial_z Q_y(k_x, k_y, z_1)\right\}e^{(z_1-z_0)\sqrt{k_x^2+k_y^2}}$$

where Z1 denotes a coordinate in the Z direction Outside the battery, and $\partial_z$ denotes a partial differential with respect to z.

4. The conductivity distribution derivation method according to claim 1,
wherein in the deriving,
the x component of the magnetic field vector and the y component of the magnetic field vector are derived based on a candidate for the conductivity distribution, a candidate for the electric potential distribution, and the plurality of relational expressions, and
when the x component derived and the y component derived fit the magnetic field indicated by the magnetic field information, the conductivity distribution is derived by determining the candidate for the conductivity distribution as the conductivity distribution.

5. The conductivity distribution derivation method according to claim 2, wherein in the deriving, the conductivity distribution is derived using a general purpose graphics processing unit (GPGPU) for using an image processing device in an application different from image processing.

6. A conductivity distribution derivation device for deriving a conductivity distribution within a battery having an electrode plate that is flat, the device comprising: an obtainment circuit configured to, while an electric current flows through a pair of electrode terminals of the battery, obtain magnetic field information indicating a magnetic field around the battery;
a derivation circuit configured to, based on a plurality of relational expressions representing a relationship of (i) an x component of a magnetic field vector in an x direction parallel to the electrode plate, (ii) a y component of the magnetic field vector in a y direction parallel to the electrode plate and perpendicular to the x direction, (iii) the conductivity distribution on a two-dimensional plane parallel to the electrode plate, and (iv) an electric potential distribution on a two-dimensional plane parallel to the electrode plate, derive the conductivity distribution that satisfies the plurality of relational expressions with respect to the magnetic field information; and
an image display device configured to display an image representing the conductivity distribution, the image representing the conductivity distribution indicating an electrical abnormality of the battery,
wherein the plurality of relational expressions include a first relational expression, a second relational expression, and a third relational expression, and
the derivation circuit is configured to derive the conductivity distribution that is represented using σ based on the first relational expression that is represented by [Math. 12], the second relational expression that is represented by [Math. 131, and the third relational expression that is represented by [Math. 14], $$\varphi \qquad \text{[Math. 11]}$$

$$\Delta H_x = h_T^{-1} h \partial_y \{\sigma(x,y)\varphi(x,y)\}\delta(z-z_0) - \sigma_0 h \{\partial_y \varphi(x,y)\}\delta'(z-z_0) \qquad \text{[Math. 12]}$$

$$\Delta H_y = -h_T^{-1} h \partial_x \{\sigma(x,y)\varphi(x,y)\}\delta(z-z_0) - \sigma_0 h \{\partial_y \varphi(x,y)\}\delta'(z-z_0) \qquad \text{[Math. 13]}$$

$$\partial_x^2 \varphi + \partial_y^2 \varphi = (\sigma_0 h h_T)^{-1} \sigma(x,y)\varphi(x,y) \qquad \text{[Math. 14]}$$

where x denotes a coordinate in the x direction, y denotes a coordinate in the y direction, z denotes a coordinate in a z direction perpendicular to the x direction and they direction, $z_0$ denotes a coordinate of the electrode plate in the z direction, Hx denotes the x component of the magnetic field vector, Hy denotes the y component of the magnetic field vector, h denotes a thickness of the electrode plate in the z direction, hT denotes a distance between one pair of electrode plates including the electrode plate, $\sigma_0$ denotes conductivity of the electrode plate, σ denotes the conductivity distribution, [Math 11] denotes the electric potential distribution, δ denotes delta function, δ' denotes a differential of the delta function, δx denotes a partial differential with respect to x, and δy denotes a partial differential with respect to y.

* * * * *